US012727845B2

(12) United States Patent
Chou et al.

(10) Patent No.: US 12,727,845 B2
(45) Date of Patent: Sep. 8, 2026

(54) WEARABLE STETHOSCOPE

(71) Applicant: Decentralized Biotechnology Intelligence Co., Ltd., Taipei City (TW)

(72) Inventors: Yao-Sheng Chou, Taipei City (TW); Wei-Sheng Su, Taipei City (TW); Hsiao-Yi Lin, Taipei City (TW)

(73) Assignee: Decentralized Biotechnology Intelligence Co., Ltd., Taipei City (TW)

( * ) Notice: Subject to any disclaimer, the term of this patent is extended or adjusted under 35 U.S.C. 154(b) by 484 days.

(21) Appl. No.: 18/128,238

(22) Filed: Mar. 30, 2023

(65) Prior Publication Data

US 2024/0188923 A1 Jun. 13, 2024

(30) Foreign Application Priority Data

Dec. 8, 2022 (TW) ................................ 111213602
Dec. 29, 2022 (TW) ................................ 111150605

(51) Int. Cl.
*A61B 7/04* (2006.01)
*A61B 5/00* (2006.01)

(52) U.S. Cl.
CPC .............. *A61B 7/04* (2013.01); *A61B 5/6804* (2013.01); *A61B 5/7203* (2013.01)

(58) Field of Classification Search
CPC ........ A61B 5/6804; A61B 5/7203; A61B 7/04
See application file for complete search history.

(56) References Cited

U.S. PATENT DOCUMENTS

| | | | | |
|---|---|---|---|---|
| 6,661,161 | B1 * | 12/2003 | Lanzo | B06B 1/0688 310/334 |
| 2018/0108440 | A1 * | 4/2018 | Stevens | G06N 3/044 |
| 2019/0125196 | A1 * | 5/2019 | Kline | A61B 5/0285 |
| 2021/0186329 | A1 * | 6/2021 | Tran | A61B 5/002 |
| 2021/0195732 | A1 * | 6/2021 | Longinotti-Buitoni | H05K 3/361 |
| 2021/0345939 | A1 * | 11/2021 | Jumbe | H04R 1/028 |

* cited by examiner

*Primary Examiner* — Amanda L Steinberg
(74) *Attorney, Agent, or Firm* — WPAT, P.C.; Anthony King

(57) ABSTRACT

A wearable stethoscope includes a clothing body, a sound sensor configured to collect heart sound signals of a user, the sound sensor having a diaphragm, a piezoelectric sensor, and a circuit board. The circuit board is electrically connected to the sound sensor and the piezoelectric sensor to preprocess the collected heart sound signals. The sound sensor is integrated with the clothing body.

20 Claims, 5 Drawing Sheets

WEARABLE STETHOSCOPE

CROSS-REFERENCE STATEMENT

The present application is based on, and claims priority from, Taiwan Patent Application Serial Number 111213602, filed Dec. 8, 2022, and Taiwan Patent Application Serial Number 111150605, filed Dec. 29, 2022, the disclosure of which are hereby incorporated by reference herein in their entirety.

TECHNICAL FIELD

The present invention relates to technology field of body sound detection device, and more particularly, a wearable stethoscope.

BACKGROUND

In recent years, wearable sensors have emerged, such as smart watches, bracelets, etc., which allow us to continuously monitor our health in a non-invasive manner.

According to the survey reports, consumers look forward to being able to integrate medical wearable devices into the equipment of their clothing. With the improvement of health awareness happened globally, the demand for medical wearable devices is also increasing. Technically, Bluetooth Low Energy (BLE) technology can be used to connect with mobile phones to record or analyze various sensing data. Uploading the sensing data to the cloud allows doctors to remotely monitor and track the health status of the elderly or patients 24 hours a day.

With the trend of population aging, heart failure is a prevalent public health problem worldwide, which constitutes a huge burden on the overall medical cost of public health system. In recent years, as people pay more attention to their health problems, improvement of health or early detection of disease can be effectively applied to people via long-term monitoring, recording and analysis of physiological information.

To early detect symptoms of cardiac disease, which has a high rate of sudden death, wearable auscultation (heart sound) devices can provide real-time and effective detection and recording for abnormal heartbeat signals. Physicians can use this real-time physiological audio information to analyze and provide health warning and healthcare solutions.

In early time, wearable medical devices are bulky, making users feel that there is a foreign body sensation while wearing them, and the battery to power the device should be replaced by users, which can cause inconvenience in life. Therefore, users resisted to wear wearable medical devices unless necessary.

Since the advent of wearable devices, medical wearable devices have developed various shapes. However, traditional medical wearable devices, such as wearable stethoscopes, are usually worn with a belt, which may cause discomfort when worn for a long time.

Therefore, it is highly desirable to propose a wearable stethoscope that can be integrated with clothes and further improve the discomfort caused by wearing a heart sound sensor in a traditional way.

SUMMARY

In one aspect of the present invention, a wearable stethoscope is proposed, which includes a clothing body, a sound sensor configured to collect heart sound signals of a user, the sound sensor having a diaphragm, a piezoelectric sensor, and a circuit board. The circuit board is electrically connected to the sound sensor and the piezoelectric sensor to preprocess the collected heart sound signals. The sound sensor is integrated with the clothing body.

In one preferred embodiment, the diaphragm is disposed on a surface of the circuit board, a soundproof ring is disposed on the surface and encloses the diaphragm to form a resonant cavity; the piezoelectric sound sensor is arranged on a side of the soundproof ring that is not in contact with the circuit board, wherein the piezoelectric sound sensor is directly attached to user's skin, or through the clothing body attached to the user's skin.

In one preferred embodiment, the piezoelectric sound sensor includes a piezoelectric layer, and upper and lower surfaces of the piezoelectric layer have conductive electrodes.

In one preferred embodiment, said sound sensor is integrated with the clothing body through a storage bag.

In one preferred embodiment, the sound sensor is detachably integrated with the clothing body through a connecting piece.

In one preferred embodiment, the connecting piece is a touch fastener, a buckle or a zipper.

In one preferred embodiment, the clothing body is a tight-fitting clothing that fits the user's body, to facilitate the piezoelectric sensor of the stethoscope sensing the user's body sounds, especially the user's heart sound signals.

In one preferred embodiment, the circuit board at least includes a signal preprocessing module comprising a filter, a signal amplifier electrically connected to the filter and an analog to digital converter electrically connected to the signal amplifier, for sequentially filtering, amplifying and digitizing the heart sound signals, and a microprocessor electrically connected to the analog to digital converter used to receive and process the digitalized heart sound signals to obtain preprocessed heart sound signals with background noise been removed.

In one preferred embodiment, the preprocessed heart sound signals are analyzed and cross-referenced with an existing database through an external electronic computing device communicatively coupled with the wearable stethoscope.

In one preferred embodiment, the external electronic computing device is a smart phone.

In another aspect of the present invention, a wearable stethoscope integrated with a clothing body is proposed, which includes a sound sensor configured to collect heart sound signals of a user, the sound sensor including a diaphragm, a piezoelectric sensor, a soundproof ring and a circuit board. The diaphragm is disposed on a surface of the circuit board, the soundproof ring is disposed on the surface and encloses the diaphragm to form a resonant cavity. The piezoelectric sound sensor is arranged on a side of the soundproof ring that is not in contact with the circuit board. The circuit board is electrically connected to the sound sensor and the piezoelectric sensor to preprocess the collected heart sound signals. The sound sensor is integrated with the clothing body.

In one preferred embodiment, the piezoelectric sound sensor is directly attached to user's skin, or through the clothing body attached to the user's skin.

In one preferred embodiment, the piezoelectric sound sensor includes a piezoelectric layer, and upper and lower surfaces of the piezoelectric layer have conductive electrodes.

In one preferred embodiment, the sound sensor is integrated with the clothing body through a storage bag.

In one preferred embodiment, the sound sensor is detachably integrated with the clothing body through a connecting piece.

In one preferred embodiment, the connecting piece is a touch fastener, a buckle or a zipper.

In one preferred embodiment, the clothing body is a tight-fitting clothing that fits the user's body, to facilitate the piezoelectric sensor of the stethoscope sensing the user's body sounds, especially for sensing the user's heart sound signals.

In one preferred embodiment, the circuit board at least includes a signal preprocessing module comprising a filter, a signal amplifier electrically connected to the filter and an analog to digital converter electrically connected to the signal amplifier, for sequentially filtering, amplifying and digitizing the heart sound signals, and a microprocessor electrically connected to the analog to digital converter, used to receive and process the digitalized heart sound signals to obtain preprocessed heart sound signals with background noise been removed.

In one preferred embodiment, the preprocessed heart sound signals are analyzed and cross-referenced with an existing database through an external electronic computing device communicatively coupled with the wearable stethoscope.

In one preferred embodiment, the external electronic computing device is a smart phone.

BRIEF DESCRIPTION OF THE DRAWINGS

The components, characteristics and advantages of the present invention may be understood by the detailed descriptions of the preferred embodiments outlined in the specification and the drawings attached.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

Consumption or medical wearable device has a variety of appearances, among which, wearable biosensors can be transformed into more diverse types, because they can appear in the form of gloves, clothes, bandages and implants, and can be utilized as non-invasive disease diagnosis and health monitoring tool.

The most important function of the wearable medical device is to detect various information of human body, so the accuracy of its internal sensors is very important.

Traditional heart sound sensing equipment is based on a heart sound probe or a cylindrical microphone sensor to collect heart sound signals. This sensor has a relatively large volume and is difficult to implement for wearable applications. Especially when exercising, it is usually inconvenient for people to carry objects. At this scenario, the convenience of the present invention and the expectations of consumers are highlighted. Therefore, the present invention has great advantages and can be integrated into sports clothes. In one embodiment, a wearable stethoscope proposed by the present invention can be pasted on the human body or clothing by means of a patch, or can be integrated with the clothing. Through the compliance and ductility of soft materials, the sensing function is implemented in a fitting manner, which can take into account both functionality and comfort, enabling that people can monitor their physiological status in a comfortable wearing manner, and achieve the function of collecting sports data in real time.

Figure 1:
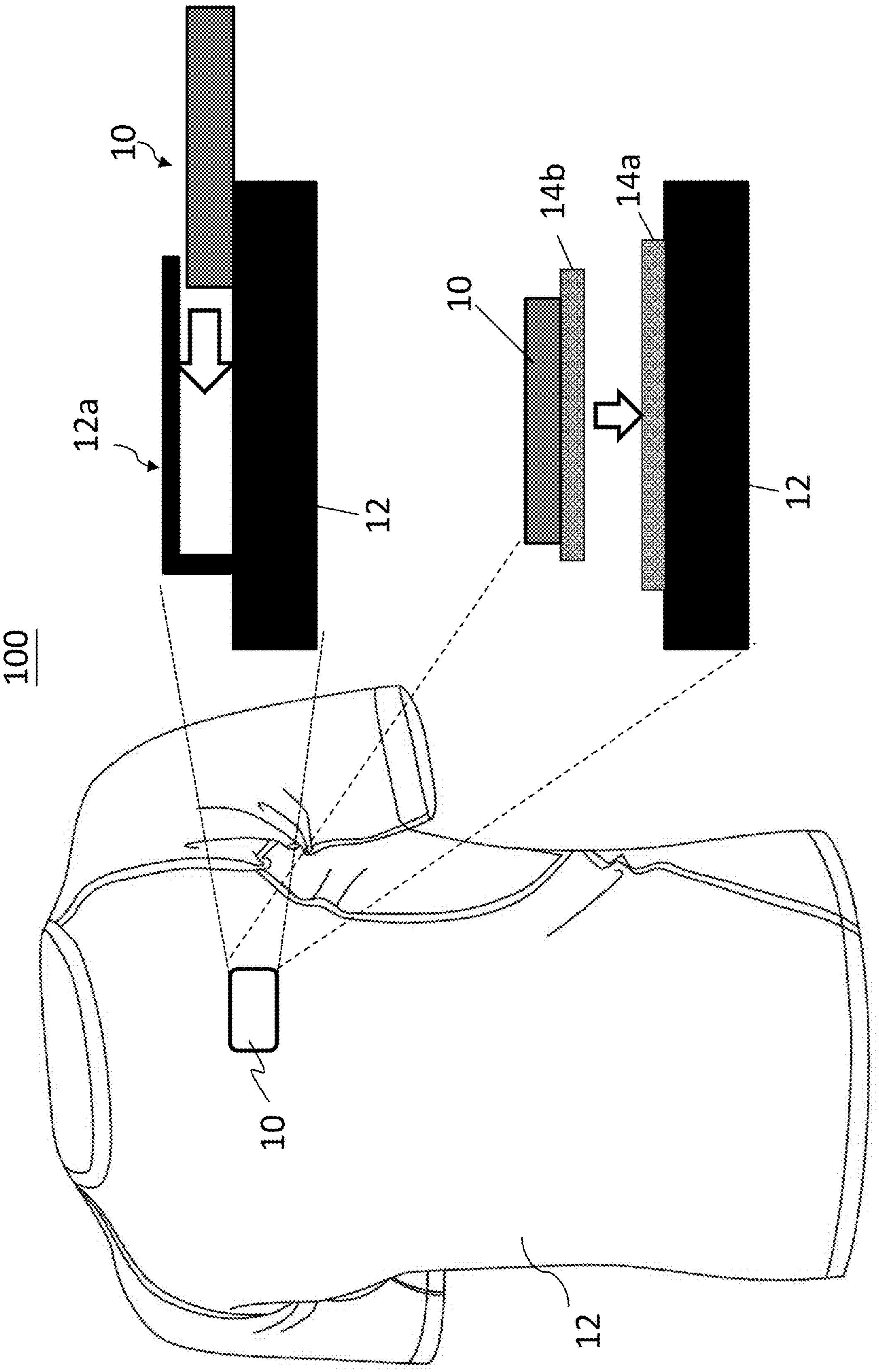
FIG. 1 shows a schematic diagram of integrating a stethoscope with clothes proposed by the present invention.

FIG. 1 shows a schematic diagram of integrating a stethoscope 10 with clothes 12 according to one embodiment of the present invention. The stethoscope 10 is a design in which a piezoelectric film is integrated into a soft substrate, and the detailed structure will be illustrated in FIG. 2. Firstly, how to integrate the stethoscope 10 with clothes will be described below.

According to an embodiment of the present invention, the stethoscope 10 can be pasted on the human body using a patch, referring to the upper right diagram of FIG. 1 again, it shows that a pocket (accommodating bag) 12*a* sewn on the clothes 12 used as an accommodating space for integrating the stethoscope 10 into the clothes, forming the wearable stethoscope 100 as a whole.

The stethoscope 10 is a detachable accessory arranged on the clothing body, for example, is arranged on the clothing body through a link, such as a buckle, a touch fastener or a zipper and the like. According to another embodiment of the present invention, refer to the lower right diagram of FIG. 1, which shows utilizing the touch fastener (14*a*, 14*b*) to attach the stethoscope 10 onto the clothes to form a wearable stethoscope 100. The touch fastener is usually composed of two fabrics, one with a loop structure (hair surface) and the other with a hook structure (hook surface). When the two pieces of fabric are pressed together firmly, the hooks and loops combine to create a temporary fastening state. To separate these two pieces, just push them apart with force. As shown in the bottom right of FIG. 1, one of the fabrics (e.g., 14*a*) of the touch fastener is sewn on the clothes 12, and the stethoscope 10 is then set firmly on the other fabric (e.g., 14*b*) of the touch fastener.

In one embodiment, the above-mentioned clothes are tight-fitting clothes that fit the body to facilitate the piezoelectric film (piezoelectric sensor) in the stethoscope 10 sensing body sounds, especially to sense heart sound signals.

Figure 2A:
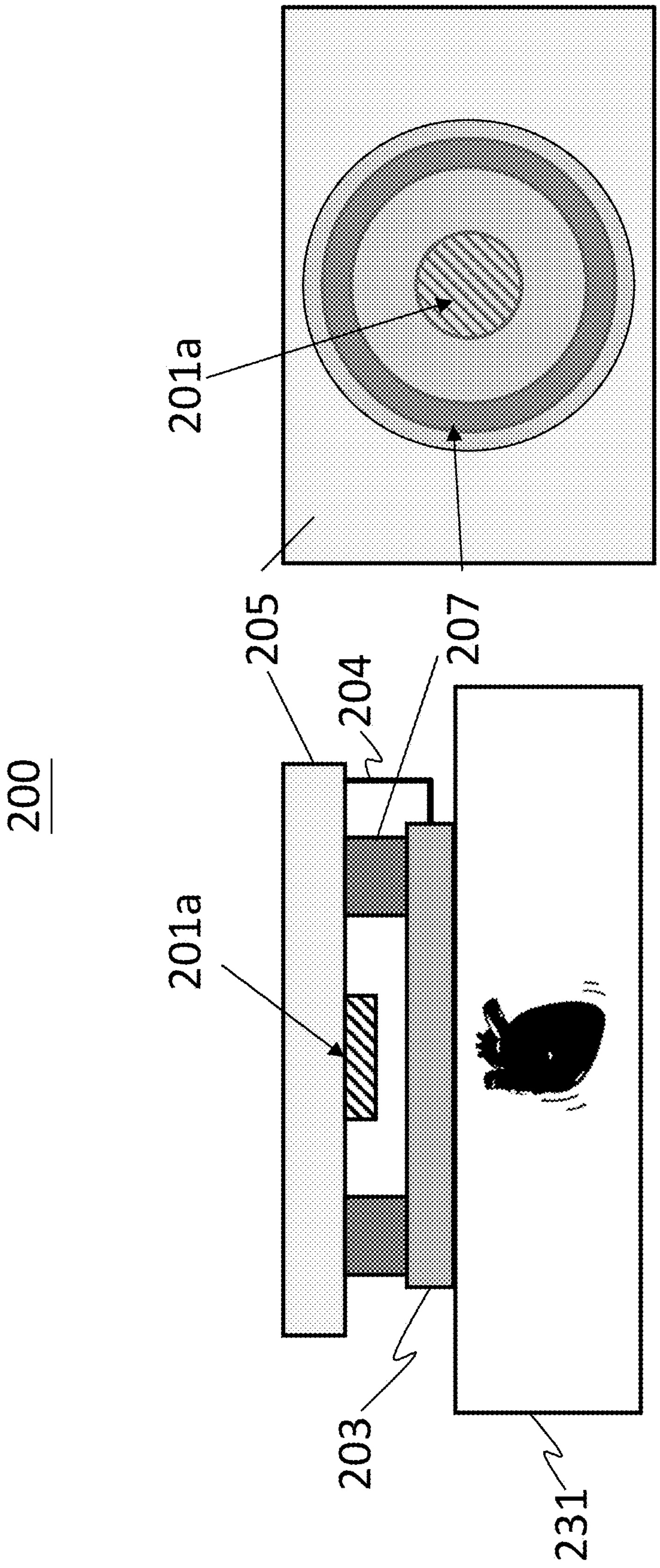
FIG. 2A shows the structure of the proposed stethoscope according to one preferred embodiment of the present invention.

FIG. 2A shows the structure of the proposed stethoscope 200 according to an embodiment of the present invention, the left figure is its cross-sectional view, and the right figure is its top view. The stethoscope 200 includes a diaphragm 201*a*, on which the diaphragm 201*a* is plated with conductive material, and the diaphragm 201*a* is packaged with a plastic frame (soundproof ring) 207 and a circuit board (hardware module 205), wherein the soundproof ring 207 and the circuit board 205 form a resonant cavity, which combined with the diaphragm 201*a* to form a microphone structure, a piezoelectric sensor 203 is arranged below the soundproof insulation ring 207, and is electrically connected to the circuit board 205 through a conductive wiring 204. The piezoelectric sensor directly or indirectly (through clothes) contacts user's skin 231 is used to measure the voltage signal generated by the vibration. That means, the piezoelectric sensor 203 can be used as a diaphragm to make up the functionality inefficiencies of the traditional capacitive sensor, which has poor response in low-frequency signals, such as the third and fourth heart sounds with frequencies around 20 Hz.

In one embodiment, the aforementioned piezoelectric sensor 203 is mainly composed of a piezoelectric material layer (for example, polyvinylidene fluoride (PVDF) polymer piezoelectric film, lead zirconate titanate (PZT) etc.) whose upper and lower surfaces are deposited with conductive metal (for example, aluminum, copper, etc.).

In one embodiment, the thickness of the piezoelectric sensor is less than 50 μm.

Figure 2C:
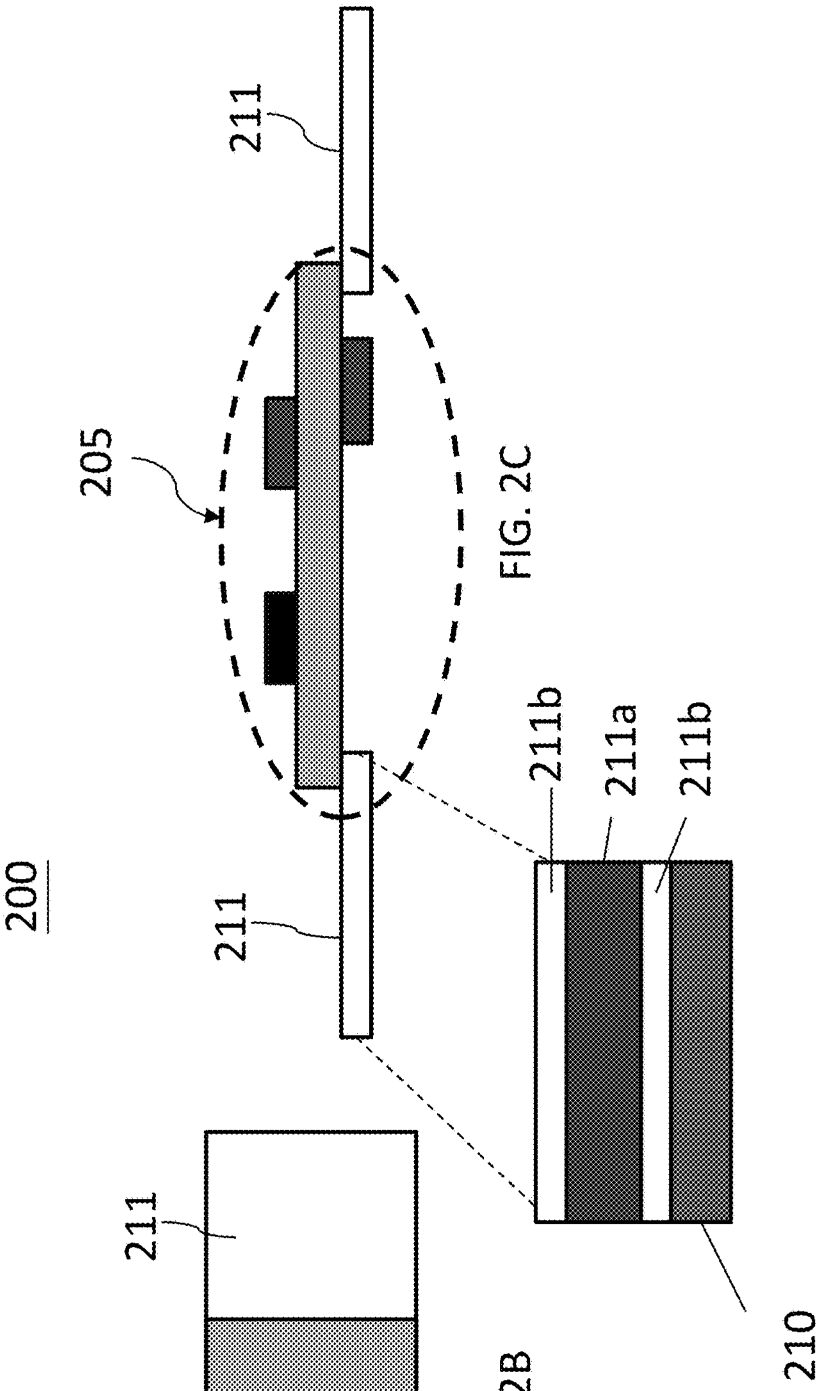
FIG. 2B-2C show the structure of the proposed stethoscope according to another embodiment of the present invention.
Figure 2B:
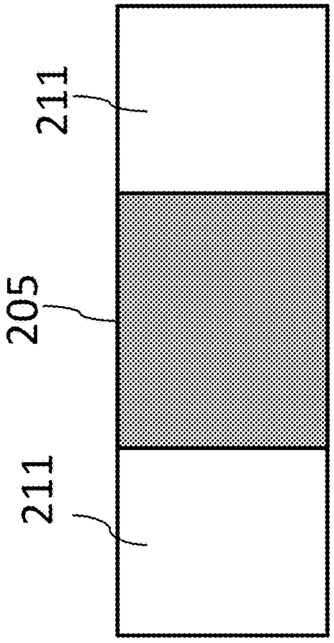

FIG. 2B-2C shows the structure of the proposed stethoscope 200 according to another embodiment of the present invention, and FIG. 2B is its top view, stethoscope 200 includes a plurality of heart sound sensors 211 and corresponding drivers and detection circuits (hardware module 205) carried by a PCB circuit board; FIG. 2C is a side view of the stethoscope 200. The PCB circuit board is equipped with processors, filters, analog/digital (A/D) converters and other electronic components to collect body sounds, such as simultaneous acquisition of body sounds at multiple points in various positions of the user's body. A plurality of heart sound signals are collected, processed and then sent to an external electronic computing device for further analysis.

In one embodiment, the heart sound sensor 211 is made of a piezoelectric layer 211*a*, such as polyvinylidene fluoride (PVDF) polymer piezoelectric film, lead zirconate titanate (PZT) and other similar materials, on which conductive metal (for example, aluminum (Al), copper (Cu), etc.) 211*b* is deposited on the upper and lower surfaces of the piezoelectric layer 211*a* as electrodes, and the piezoelectric patch formed on the flexible substrate 210 is used to sense the voltage signal generated by vibrations.

Figure 3:
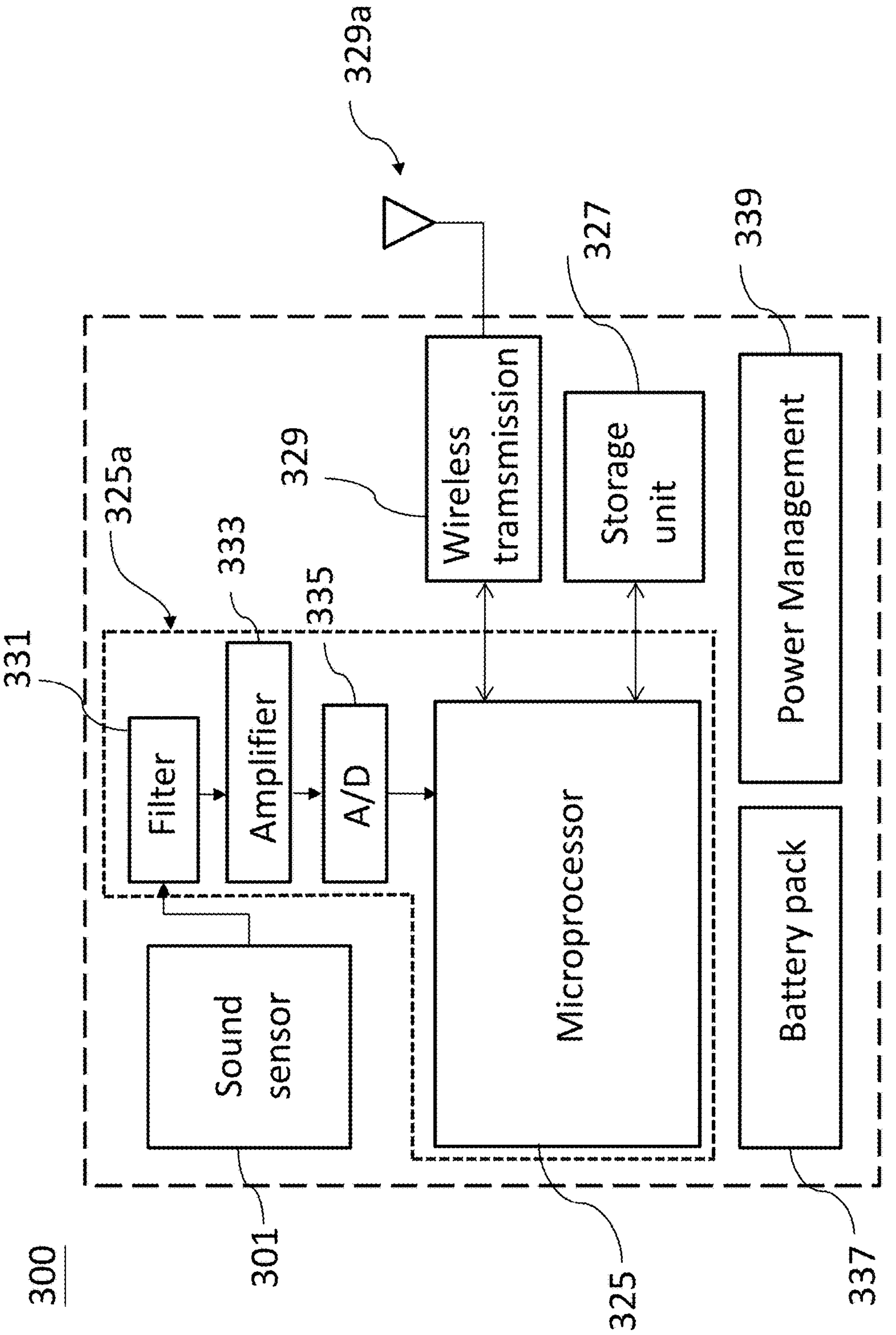
FIG. 3 illustrates the functional block diagram of the proposed stethoscope according to one embodiment of the present invention.

The wearable stethoscope 300 includes a plurality of heart sound sensors 301 and hardware modules integrated on the clothing, and its functional block diagram is shown in FIG. 3. The wearable stethoscope 300 can obtain body sounds from the human body through individual sound sensor 301 respectively, and can be configured as an auscultation device for monitoring physiological data and remote diagnosis. The wearable stethoscope 300 can receive and send data, and execute software applications, which includes at least a microprocessor, a storage unit, and a wireless transmission module.

The microprocessor 325 may be a microcontroller, a digital signal processor (DSP), an application-specific integrated circuit (ASIC), a programmable logic circuit, or other digital data processing device that can execute instructions to perform processing operations according to the present invention. The microprocessor 325 can execute various application programs stored in the storage unit.

The storage unit 327 may include read only memory (ROM), random access memory (RAM), electrically erasable programmable ROM (EEPROM), flash memory, or any memory commonly used in computers.

The wireless transmission module 329 is connected to the antenna 329*a*, and the antenna 329*a* is configured to transmit output data and receive input data through a wireless communication channel. The wireless communication channel can be a digital wireless communication channel, such as WiFi, Bluetooth, RFID, NFC, 3G/4G/5G or any other future wireless communication interface.

The body sound signals are obtained from the human body through the sound sensor 301, the noise is filtered by the filter 331, and the signal is amplified by the signal amplifier 333. The filtered and amplified body sound signals pass through an analog-to-digital converter (ADC) 335, which converts the analog sound signals into digital sound signals, and then processed by the microprocessor 325 to obtain de-noising and stable ECG signals and body sound signals. The microprocessor 325 can store the above-mentioned de-noising and stable body sound signals in the storage unit through instructions or programs, or send the above-mentioned signals to a mobile device, such as smart phone, through the wireless transmission module 329 for further analysis.

The battery pack 337 provides power for the above-mentioned wearable stethoscope 300, and can cooperate with the power management unit 339 to optimize power utilization of the wearable stethoscope 300.

The filter 331, the signal amplifier 333, the analog-to-digital converter 335 and the microprocessor 325 can be integrated into an integrated circuit (IC) as the processing unit 325*a* of the wearable stethoscope 300.

The processing unit 325*a* combines the wireless transmission module 329, the storage unit 327, the battery pack 337 and the power management unit 339 as the hardware module (or system circuit board) of the wearable stethoscope 300.

The filter 331, the signal amplifier 333, and the analog-to-digital converter 335 can be used as a preprocessing module for sequentially filtering, amplifying, and digitizing the plurality of heart sound signals.

Flexible electronics refers to the use of thin-film or direct-injection metal printing to create electronic circuits instead of silicon-based circuit production methods applied in the past. This technology can produce bendable circuits, direct-injection circuits, or organic-based materials manufactured circuits, and can meet the needs of folding and waterproofing.

According to an embodiment of the present invention, a plurality of sound sensors 301 can be disposed on a soft substrate, such as plastics, fabric, polyimide (PI), or polyethylene terephthalate (PET). It can be incorporated with the performances of semiconductor devices and printed electronics having thin, light, large-area, and flexible characteristics. Soft electronics can convert the medical apparatus into a suitable form for patient to wearing on, improve the accuracy of physiological data collection, and help doctors to understand the patient's condition more accurately and provide suitable treatments.

The sensing function is performed through the compliance and extensibility of the soft electronics on the device, which allows the device to take into account functionality, durability, and comfort at the same time, so that the patient can wear it comfortably. Real-time monitoring and recording of body information can be achieved by wearing a wearable medical device.

Facing an aging society, an immediate and preventive medical system is urgently needed to be established, among which the application of wearable devices is indispensable.

Figure 4:
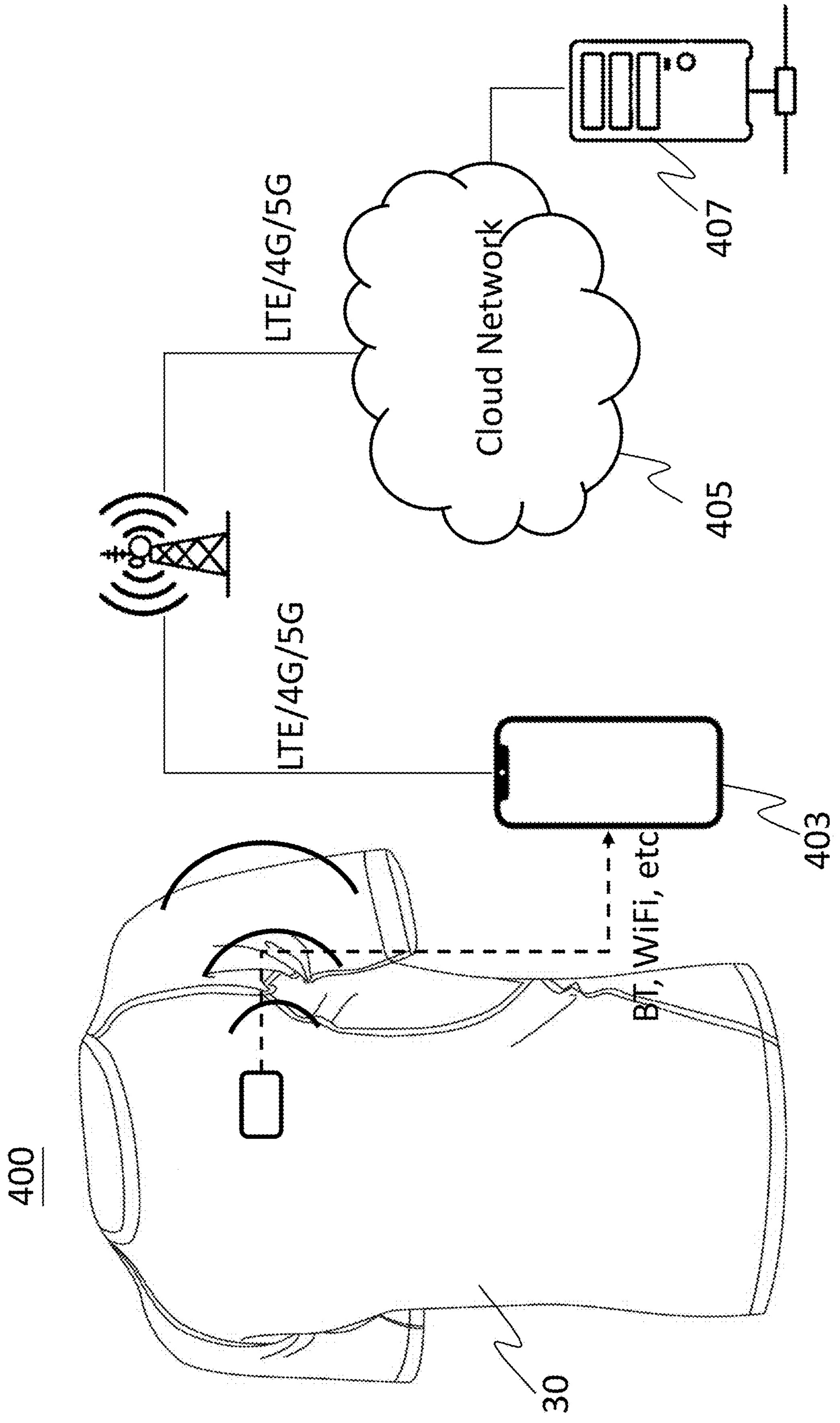
FIG. 4 illustrates a system framework illustrating physiological data transferring between the wearable stethoscope and a cloud server proposed by the present invention.

As shown in FIG. 4, a system framework illustrating physiological data transfers between the wearable stethoscope 400 and a cloud server. The wearable stethoscope 400 includes a plurality of heart sound sensors and a system circuit board 203 (refer to FIGS. 2-3), which are integrated on the user's clothes 30, and can communicatively connect with mobile devices (such as, smart phone, tablet computer and other external electronic computing devices) 403. The heart sound data collected by the heart sound signal sensors of the wearable stethoscope 400 can be uploaded to the cloud server 407 by the mobile device 403 through wireless transmission (for example, wireless communication methods such as Bluetooth and WiFi) via cloud network 405. In cloud server 407, the collected heart sound data will be stored in the cloud data database. The above system also includes an application program installed in the mobile device, the application program includes instructions for receiving and sending data between the wearable stethoscope 400, the mobile device 403 and the cloud server 405.

In one embodiment, the application program can be operated based on the Android, Windows 10 or iOS operating system platform, and the collected data/signals, such as ECG signals, heart sound signals and their waveforms, can be uploaded to the cloud server 407 for storage, and the collected data/signals are analyzed, processed and cross-referenced with an existing database through data analysis and feature extraction algorithms to generate an evaluation report and provide medical advice accordingly.

With the rapid advancement of the Internet of Things (IoTs) technology, large amounts of medical information can be exchanged and analyzed, and becomes the basis of big data in healthcare analytics. In addition, artificial intelligence, which has developed rapidly in recent years, is also imported as an inductive use of this data. After the combination of the Internet of Things and artificial intelligence, instant and mobile medical care are emerged.

The wearable device can detect the physiological condition of the patient and then make the most suitable processing and support, through real-time perception, and a large amount of data comparison and analysis, and subsequent summarization, interpretation and response. Smart medical care can be applied to physiological monitoring and general home health care. In addition, it can combine the software of smart phone and tablet computer to analyze and manage the collected physiological information (such as activity level, sleep quality, etc.), and at the same time interacts with the cooperated medical and nursing systems through wireless transmission to solve many difficulties faced by the present medical system.

While various embodiments of the present invention have been described above, it should be understood that they have been presented by a way of example and not limitation. Numerous modifications and variations within the scope of the invention are possible. The present invention should only be defined in accordance with the following claims and their equivalents.

What is claimed is:

1. A wearable stethoscope comprising:

a sound sensor configured to collect heart sound signals of a user, said sound sensor including:
 a soundproof ring having a first side and a second side opposite to said first side;
 a circuit board disposed on said first side of said soundproof ring:
 a diaphragm disposed on a first surface of said circuit board; and
 a piezoelectric sensor arranged on said second side of said soundproof ring to form a resonant cavity sealed by said soundproof ring, said first surface of said circuit board, and a second surface of said piezoelectric sensor, wherein said circuit board is electrically connected to said piezoelectric sensor to preprocess said collected heart sound signals, and wherein said diaphragm is enclosed in said resonant cavity.

2. The wearable stethoscope of claim 1, wherein said piezoelectric sensor is directly attached to user's skin, or through a clothing body attached to said user's skin.

3. The wearable stethoscope of claim 2, wherein said piezoelectric sensor includes a piezoelectric layer, and upper and lower surfaces of said piezoelectric layer have conductive electrodes.

4. The wearable stethoscope of claim 2, wherein said sound sensor is integrated with said clothing body through a storage bag.

5. The wearable stethoscope of claim 2, wherein said sound sensor is detachably integrated with said clothing body through a connecting piece.

6. The wearable stethoscope of claim 5, wherein said connecting piece is a touch fastener, a buckle or a zipper.

7. The wearable stethoscope of claim 2, wherein said clothing body is a tight-fitting clothing that fits said user's body, to facilitate said piezoelectric sensor of said stethoscope sensing said user's body sounds, especially for sensing said user's heart sound signals.

8. The wearable stethoscope of claim 1, wherein said circuit board at least includes:

a signal preprocessing module comprising a filter, a signal amplifier electrically connected to said filter and an analog to digital converter electrically connected to said signal amplifier, for sequentially filtering, amplifying and digitizing said heart sound signals;

a microprocessor, electrically connected to said analog to digital converter, used to receive and process said digitalized heart sound signals to obtain preprocessed heart sound signals with background noise been removed.

9. The wearable stethoscope of claim 8, wherein said preprocessed heart sound signals are analyzed and cross-referenced with an existing database through an external electronic computing device communicatively coupled with said wearable stethoscope.

10. The wearable stethoscope of claim 9, wherein said external electronic computing device is a smart phone.

11. A wearable stethoscope comprising:

a sound sensor configured to collect heart sound signals of a user, said sound sensor including:
 a soundproof ring having a first side and a second side opposite to said first side;
 a circuit board disposed on said first side of said soundproof ring;
 a diaphragm disposed on a first surface of said circuit board; and
 a piezoelectric sensor arranged on said second side of said soundproof ring to form a resonant cavity sealed by said soundproof ring, said first surface of said circuit board, and a second surface of said piezoelectric sensor, wherein said enclosed in said resonant cavity, wherein said circuit board is electrically connected to said piezoelectric sensor to preprocess said collected heart sound signals, and wherein said sound sensor is integrated with a clothing body.

12. The wearable stethoscope integrated with a clothing body of claim 11, wherein said piezoelectric sensor is directly attached to user's skin, or through said clothing body attached to said user's skin.

13. The wearable stethoscope integrated with a clothing body of claim 12, wherein said piezoelectric sensor includes a piezoelectric layer, and upper and lower surfaces of said piezoelectric layer have conductive electrodes.

14. The wearable stethoscope integrated with a clothing body of claim 12, wherein said sound sensor is integrated with said clothing body through a storage bag.

15. The wearable stethoscope integrated with a clothing body of claim 12, wherein said sound sensor is detachably integrated with said clothing body through a connecting piece.

16. The wearable stethoscope integrated with a clothing body of claim 15, wherein said connecting piece is a touch fastener, a buckle or a zipper.

17. The wearable stethoscope integrated with a clothing body of claim 12, wherein said clothing body is a tight-fitting clothing that fits said user's body, to facilitate said piezoelectric sensor of said stethoscope sensing said user's body sounds, especially for sensing said user's heart sound signals.

18. The wearable stethoscope integrated with a clothing body of claim 11, wherein said circuit board at least includes:

a signal preprocessing module comprising a filter, a signal amplifier electrically connected to said filter and an analog to digital converter electrically connected to said signal amplifier, for sequentially filtering, amplifying and digitizing said heart sound signals;

a microprocessor, electrically connected to said analog to digital converter, used to receive and process said digitalized heart sound signals to obtain preprocessed heart sound signals with background noise been removed.

19. The wearable stethoscope integrated with a clothing body of claim 18, wherein said preprocessed heart sound signals are analyzed and cross-referenced with an existing database through an external electronic computing device communicatively coupled with said wearable stethoscope.

20. The wearable stethoscope integrated with a clothing body of claim 19, wherein said external electronic computing device is a smart phone.

* * * * *